(12) United States Patent
Ikeguchi

(10) Patent No.: US 10,501,409 B2
(45) Date of Patent: Dec. 10, 2019

(54) METHOD FOR PRODUCING METHIONINE AND/OR 2-HYDROXY-4-(METHYLTHIO) BUTANOIC ACID

(71) Applicant: SUMITOMO CHEMICAL COMPANY, LIMITED, Tokyo (JP)

(72) Inventor: Masayuki Ikeguchi, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/124,764

(22) Filed: Sep. 7, 2018

(65) Prior Publication Data

US 2019/0077750 A1 Mar. 14, 2019

(30) Foreign Application Priority Data

Sep. 8, 2017 (JP) ................................ 2017-172739

(51) Int. Cl.
- *C07C 319/20* (2006.01)
- *C07C 323/58* (2006.01)
- *B01J 23/10* (2006.01)

(52) U.S. Cl.
CPC ............. *C07C 319/20* (2013.01); *B01J 23/10* (2013.01); *B01J 2523/3712* (2013.01)

(58) Field of Classification Search
CPC ...... C07C 319/12; C07C 319/20; B01J 23/10; B01J 2523/3712
See application file for complete search history.

(56) References Cited

U.S. PATENT DOCUMENTS

| 2003/0092934 A1 | 5/2003 | Ikudome et al. |
| 2010/0121104 A1 | 5/2010 | Azemi et al. |
| 2010/0197965 A1* | 8/2010 | Belliere-Baca .......... B01J 23/10 562/606 |
| 2017/0275247 A1 | 9/2017 | Matsumura |

FOREIGN PATENT DOCUMENTS

| FR | 2 405 924 A1 | 5/1979 | |
| JP | 2002-105048 * | 4/2002 | ........... C07C 319/20 |
| JP | 3932757 B2 | 6/2007 | |
| JP | 2010-111642 A | 5/2010 | |
| WO | 2016/047516 A1 | 3/2016 | |

OTHER PUBLICATIONS

Holland et al., "Experiments in the Synthesis of Methionine", Journal of the Chemical Society, Chemical Society, XP000652690, Jan. 1, 1952, pp. 3403-3409.
Search Report issued in European Patent Application No. 18192569.4, dated Feb. 12, 2019.

* cited by examiner

*Primary Examiner* — Rosalynd A Keys
(74) *Attorney, Agent, or Firm* — Birch, Stewart, Kolasch & Birch, LLP

(57) ABSTRACT

An object of the invention is to provide a simple method for producing methionine and/or 2-hydroxy-4-(methylthio)butanoic acid at a high yield using 3-(methylthio)propionaldehyde as a raw material. An oxide catalyst containing cerium, 3-(methylthio)propionaldehyde, a compound containing cyanide ion, ammonia or a compound containing ammonium ion, and water are contacted with each other to produce methionine and/or 2-hydroxy-4-(methylthio)butanoic acid.

8 Claims, No Drawings

METHOD FOR PRODUCING METHIONINE AND/OR 2-HYDROXY-4-(METHYLTHIO) BUTANOIC ACID

TECHNICAL FIELD

The present invention relates to a method for producing methionine and/or 2-hydroxy-4-(methylthio)butanoic acid using 3-(methylthio)propionaldehyde as a raw material.

BACKGROUND ART

Methionine and 2-hydroxy-4-(methylthio)butanoic acid (which may hereinafter also be referred to as "liquid methionine") are both useful as an additive for animal feed. Methionine and liquid methionine are produced by using 3-(methylthio)propionaldehyde as a raw material.

As a method for producing methionine, for example, Patent Document 1 discloses a method for obtaining methionine, the method comprising obtaining 2-hydroxy-4-(methylthio)butanenitrile by reacting 3-(methylthio)propionaldehyde with hydrogen cyanide in the presence of a base, then reacting the resulting 2-hydroxy-4-(methylthio)butanenitrile with ammonium carbonate to give 5-(β-methylmercaptoethyl)hydantoin, followed by hydrolysis in the presence of a basic potassium compound to obtain methionine.

Patent Document 2 discloses a method for producing methionine at a high yield, the method comprising obtaining 2-amino-4-(methylthio)butanenitrile by reacting 3-(methylthio)propionaldehyde, hydrogen cyanide, and ammonia, and contacting the obtained 2-amino-4-(methylthio)butanenitrile with water in the presence of an oxide catalyst containing cerium.

As a method for producing liquid methionine, for example, Patent Document 3 discloses a method for obtaining liquid methionine, the method comprising reacting 3-(methylthio)propionaldehyde with hydrogen cyanide, followed by hydrolysis of the resulting 2-hydroxy-4-(methylthio)butanenitrile in the presence of sulfuric acid.

CITATION LIST

Patent Documents

Patent Document 1: JP2010-111642A
Patent Document 2: WO2016/047516
Patent Document 3: Japanese Patent No. 3932757

SUMMARY OF INVENTION

Problem to be Solved by the Invention

All of the methods for producing methionine and liquid methionine disclosed in Patent Documents 1 to 3 had problems to be solved, such as a high operation cost and high facility cost due to multiple manufacturing steps. Therefore, an object of the present invention is to provide a simple method for producing methionine and/or 2-hydroxy-4-(methylthio)butanoic acid at a high yield using 3-(methylthio)propionaldehyde as a raw material.

Means for Solving the Problem

The inventor of the present invention carried out extensive research, and found that, by contacting an oxide catalyst containing cerium; 3-(methylthio)propionaldehyde; a compound containing cyanide ion; ammonia or a compound containing ammonium ion; and water with each other, it is possible to produce methionine and/or 2-hydroxy-4-(methylthio)butanoic acid at a high yield with a single-stage reaction from 3-(methylthio)propionaldehyde. With further consideration based on this finding, the inventor completed the present invention.

More specifically, the present invention encompasses the following items.

[1] A method for producing methionine and/or 2-hydroxy-4-(methylthio)butanoic acid, comprising contacting an oxide catalyst containing cerium, 3-(methylthio)propionaldehyde, a compound containing cyanide ion, ammonia or a compound containing ammonium ion, and water with each other.

[2] The method according to Item [1], wherein the oxide catalyst containing cerium is at least one oxide selected from cerium oxides and oxide solid solutions containing cerium.

[3] The method according to Item [1] or [2], wherein the compound containing cyanide ion is hydrogen cyanide.

[4] The method according to any one of Items [1] to [3], wherein ammonia or the compound containing ammonium ion is at least one member selected from aqueous ammonia, liquid ammonia, and ammonia gas.

[5] The method according to any one of Items [1] to [4], wherein the reaction temperature is 40 to 110° C.

[6] The method according to any one of Items [1] to [5], wherein the oxide catalyst containing cerium, 3-(methylthio) propionaldehyde, hydrogen cyanide, ammonia, and water are contacted with each other in a single vessel.

[7] The method according to any one of Items [1] to [6], wherein the oxide catalyst containing cerium and 3-(methylthio)propionaldehyde are contacted with each other in the presence of the compound containing cyanide ion and ammonia or the compound containing ammonium ion.

[8] The method according to any one of Items [1] to [7], wherein, after the oxide catalyst containing cerium, the compound containing cyanide ion, ammonia or the compound containing ammonium ion, and water are mixed, the mixture is mixed with 3-(methylthio)propionaldehyde.

Advantageous Effects of Invention

The production method of the present invention enables simple production of methionine and/or 2-hydroxy-4-(methylthio)butanoic acid at a high yield using 3-(methylthio) propionaldehyde as a raw material.

In contrast to the previously-known methods for producing methionine or liquid methionine that required two or more manufacturing steps (Patent Documents 2 and 3), the production method of the present invention may be performed with a single manufacturing step; therefore, the handleability can be significantly increased, and the operation and facility costs may be greatly reduced.

Further, the present inventors had uniquely found the following improvements over the methionine production method requiring two manufacturing steps (Patent Document 2). Specifically, in the previously-known method, a separation device and a storage facility were required because the liquid containing 2-amino-4-(methylthio)butanenitrile, which is a temporarily produced intermediate, was separated into oil and water; further, since 2-amino-4-(methylthio)butanenitrile is unstable both thermally and over time, by-products were unavoidably generated due to decomposition. However, since the production method of the present invention may be performed with a single manufacturing step, the separation device and the storage facility are not necessary, and the generation of by-products may be greatly reduced, thereby obtaining the desired methionine and/or 2-hydroxy-4-(methylthio)butanoic acid at a high yield.

DESCRIPTION OF EMBODIMENTS

The production method of the present invention comprises contacting an oxide catalyst containing cerium; 3-(methylthio)propionaldehyde; a compound containing cyanide ion; ammonia or a compound containing ammonium ion; and water, with each other, thereby producing methionine and/or 2-hydroxy-4-(methylthio)butanoic acid at a high yield with a single manufacturing step from 3-(methylthio)propionaldehyde.

In the production method of the present invention, the reaction path in the reaction system from 3-(methylthio) propionaldehyde (1) as a raw material to methionine (4) and/or 2-hydroxy-4-(methylthio)butanoic acid (7) as target products with a single manufacturing step is as follows.
Reaction Formula in an industrial scale. Further, since the production method of the present invention does not perform an operation for obtaining a liquid containing 2-amino-4-(methylthio)butanenitrile (2), a separation device and a storage facility are not necessary, and therefore it is economical.

Still further, since the production method of the present invention enables the production of the target compound, i.e., methionine (4) and/or 2-hydroxy-4-(methylthio)butanoic acid (7), without obtaining 2-amino-4-(methylthio) butanenitrile (2), it is possible to greatly reduce the generation of by-products, thereby obtaining the target compound at a high yield.

In the production method of the present invention, as shown in the reaction formula above, 2-amino-4-(methylthio)butanamide (3) and 2-hydroxy-4-(methylthio)butanamide (6), which are precursors (intermediates) of methionine (4) and/or 2-hydroxy-4-(methylthio)butanoic acid (7), are generated in some cases. The compounds (3) and (6) may be reduced by adjusting the reaction time, the reaction

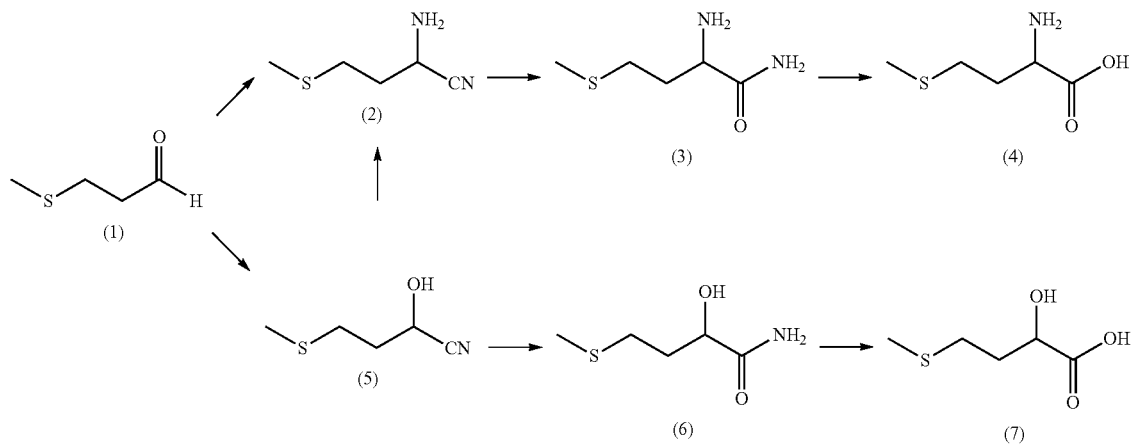

The methionine (4) production path is such that 2-amino-4-(methylthio)butanenitrile is first produced from the raw material, i.e., 3-(methylthio)propionaldehyde (1); 2-amino-4-(methylthio)butanamide (3) is subsequently produced by hydration; and then methionine (4) is produced by hydrolysis.

The 2-hydroxy-4-(methylthio)butanoic acid (7) production path is such that 2-hydroxy-4-(methylthio)butanenitrile (5) is first produced from the raw material, i.e., 3-(methylthio)propionaldehyde (1); 2-hydroxy-4-(methylthio)butanamide (6) is subsequently produced by hydration; and then 2-hydroxy-4-(methylthio)butanoic acid (7) is produced by hydrolysis.

The production method of the present invention enables production of the target products, i.e., methionine (4) and/or 2-hydroxy-4-(methylthio)butanoic acid (7) at a high yield with a single manufacturing step from the raw material, i.e., 3-(methylthio)propionaldehyde (1).

Since the production method of the present invention may be performed with a single manufacturing step, compared with previously-known methods that required two or more manufacturing steps, the handleability can be significantly increased, and the operation and facility costs may be greatly reduced. In particular, the production method of the present invention is significantly useful in the production of methionine (4) and/or 2-hydroxy-4-(methylthio)butanoic acid (7)

temperature, or the like (generally, by increasing the reaction temperature and prolonging the reaction time), thereby facilitating the reaction. Alternatively, the compounds (3) and (6) may be separated from the target compounds (4) and (7) after the reaction, and recycled in the production method of the present invention. As is clear from the above, the compounds (3) and (6) may be regarded as useful components (hereinafter referred to as "valuable components") as precursors (intermediates) of the target compounds (4) and (7).

The production method of the present invention generally yields a mixture of methionine (4) and 2-hydroxy-4-(methylthio)butanoic acid (7). Since methionine (4) and 2-hydroxy-4-(methylthio)butanoic acid (7) exhibit similar effects as a feed additive, they are useful both alone and as a mixture.

Methionine (4) and 2-hydroxy-4-(methylthio)butanoic acid may be separated and/or purified from the above mixture. The separation and/or purification methods are not particularly limited, and examples include crystallization, condensation, extraction, distillation, oil/water separation, neutralization, filtration, chromatography, and the like.

For example, by removing an oxide catalyst containing cerium (in particular, cerium oxide) from a reaction fluid containing the mixture, condensing and cooling the reaction fluid to crystallize methionine, and filtering the crystal, followed by washing, a solid of methionine (4) is obtained. By recrystallizing the solid as necessary, methionine (4) having high purity is obtained. Further, by condensing the filtrate obtained by filtration, 2-hydroxy-4-(methylthio)butanoic acid (7) having a high concentration is obtained.

The oxide catalyst containing cerium (Ce) used in the present invention contains, for example, an oxide containing cerium (Ce) (e.g., cerium oxide, oxide solid solution or mixed oxide containing cerium, etc.). Examples thereof also include catalysts in which other components are supported by the oxide containing cerium that serves as a support and catalysts in which the oxide containing cerium is supported by a support. Among these oxide catalysts containing cerium (Ce), cerium oxide and oxide solid solutions containing cerium are preferable, and cerium oxide is most preferable.

Examples of cerium oxide include cerium(III) oxide ($Ce_2O_3$), cerium(IV) oxide ($CeO_2$), and mixed phases thereof; among these, cerium(IV) oxide $CeO_2$ is preferable.

Examples of the oxide solid solution containing cerium include $CeO_2$—$ZrO_2$ (ceria-zirconia), $CeO_2$—$Y_2O_3$, $CeO_2$—$La_2O_3$, and the like. The component to be solid-soluted with cerium oxide is not limited, and it may contain three or more metals. Among these, ceria-zirconia is most preferable.

Examples of the mixed oxide containing cerium include $CeAlO_3$, $CeGaO_3$, $CeFeO_3$, $CeCrO_3$, $CeScO_3$, $MgCeO_3$, $CaCeO_3$, $SrCeO_3$, $BaCeO_3$ and the like. Each metal element may be partially replaced by another element.

In the oxide catalyst containing cerium, the content of cerium is, as the content of cerium(IV) oxide, preferably 5 to 100 wt %, more preferably 30 to 100 wt %, further preferably 70 to 100 wt %, and most preferably 95 to 100 wt %.

The oxide catalyst containing cerium may be used by being mixed with other catalysts. The other catalysts are not particularly limited, and examples include zirconium oxide, magnesium oxide, zinc oxide, titanium oxide, and like oxides; and hydrotalcite and like clay minerals. Among these, zirconium oxide is preferable. In this case, the content of oxide catalyst containing cerium is preferably 50 to 100 wt % in the entire catalyst.

As the oxide catalyst containing cerium, two or more catalysts different in composition and physical property (form, particle size, etc.) may be used in combination. The average primary particle size of the oxide containing cerium in the oxide catalyst containing powdery cerium is preferably 500 nm or less, more preferably 100 nm less, and further preferably 20 nm or less; preferably 0.5 nm or more, and more preferably 1 nm or more. The average primary particle size of the catalyst is measured using a transmission electron microscope (TEM), a scanning electron microscope (SEM), or a like electron microscope.

The oxide catalyst containing cerium may be any commercially available catalyst, or may be produced according to or by referring to a known method. The oxide catalyst containing cerium may be prepared, for example, by a method of calcining a precursor containing a cerium compound under an atmosphere of oxidizing gases, such as air. Examples of cerium compounds include halides, inorganic salts (e.g., sulfates, nitrates, carbonates, phosphates), acetates, oxalates, hydroxides, and the like, of cerium.

The oxide catalyst containing cerium may be activated by heating using an oxidizing gas, such as air, an inert gas, such as nitrogen or argon, a reducing gas, such as hydrogen, carbon dioxide, or steam. The heating temperature is not particularly limited, the heating temperature is preferably 200 to 1200° C., and more preferably 400 to 1100° C.

The form of the oxide catalyst containing cerium is not particularly limited. A catalyst processed into a formed product, such as a pellet or the like, may be used if necessary. The formed product may be prepared, for example, by a method comprising adding water or the like to a powdery compound containing cerium, and a solid support, which may be used if necessary, thereby obtaining a paste, then obtaining a formed product such as a pellet-like formed product through extrusion, and calcining the resulting extruded product.

The amount of the oxide catalyst containing cerium is, in a cerium amount, generally 0.001 to 5 moles, more preferably 0.01 to 3 moles, further preferably 0.02 to 1.5 moles, per mole of 3-(methylthio)propionaldehyde.

Examples of compounds containing cyanide ion include hydrogen cyanide, sodium cyanide, potassium cyanide, silver cyanide, copper cyanide, zinc cyanide, ammonium cyanide, and the like. One or more compounds among these compounds may be used. Of these, in terms of being free of metal ions and no need for separation and removal of metal ions in the subsequent step, hydrogen cyanide and ammonium cyanide are preferable, and hydrogen cyanide is most preferable. Hydrogen cyanide may be supplied as a liquid, may be blown into a liquid as a gas, or may be supplied as an aqueous solution.

The amount of the compound containing cyanide ion is generally 0.01 to 100 moles, more preferably 0.9 to 10 moles, most preferably 1.0 to 3 moles, per mole of 3-(methylthio) propionaldehyde.

Examples of ammonia or the compound containing ammonium ion include aqueous ammonia, liquid ammonia, ammonia gas, ammonium carbonate, ammonium hydrogen carbonate, ammonium acetate, ammonium formate, ammonium nitrate, ammonium sulfate, ammonium fluoride, ammonium chloride, ammonium bromide, ammonium iodide, ammonium dihydrogenphosphate, ammonium borate, ammonium tartrate, ammonium oxalate, and the like. One or more substances among these substances may be used. Among these, aqueous ammonia, liquid ammonia, or ammonia gas is preferable, and aqueous ammonia is most preferable in terms of easy handling.

The amount of ammonia or the compound containing ammonium ion is generally 0.01 to 100 moles, per mole of 3-(methylthio)propionaldehyde. The amount of ammonia or the compound containing ammonium ion is preferably greater to obtain a greater amount of methionine (4). The amount is preferably 1.5 to 100 moles, more preferably 2 to 10 moles (e.g., see Example 3). In contrast, the amount of ammonia or the compound containing ammonium ion is preferably smaller to obtain a greater amount of 2-hydroxy-4-(methylthio)butanoic acid (7). The amount is preferably 0.01 to 1.5 moles (e.g., see Example 2).

The amount of water (when aqueous ammonia or the like is used as a raw material, the amount also includes water contained in the raw material) is generally 2 to 1000 moles, more preferably 5 to 100 moles, and most preferably 10 to 50 moles, per mole of 3-(methylthio)propionaldehyde.

The production method of the present invention generally uses water in the solvent amount; however, as necessary, an organic solvent, which may be mixed or not mixed with water, may be used. Examples of the solvents to be mixed with water include methanol, ethanol, isopropanol, or like alcohol solvents, 1,4-dioxane, tetrahydrofuran, or like ether solvents, acetonitrile, acetone, dimethylsulfoxide, N-methylpyrrolidinone, N-ethylpyrrolidinone, 1,3-dimethyl-2-imidazolidinone, and the like.

In the production method of the present invention, an oxide catalyst containing cerium, 3-(methylthio)propionaldehyde, a compound containing cyanide ion, ammonia or a compound containing ammonium ion, and water are contacted with each other. The procedures for contacting or mixing the components are explained below. For example, it is possible that, after the oxide catalyst containing cerium is mixed with water, the compound containing cyanide ion and ammonia or the compound containing ammonium ion are added, and, finally, 3-(methylthio)propionaldehyde is added. Further, it is also possible that, after the compound containing cyanide ion is mixed with ammonia or the compound containing ammonium ion, the oxide catalyst containing cerium is added, then 3-(methylthio)propionaldehyde is added, and, finally, water is added. Further, it is also possible that the oxide catalyst containing cerium is added to 3-(methylthio)propionaldehyde, water is added thereto, then ammonia or the compound containing ammonium ion is added, and the compound containing cyanide ion is mixed.

Among these, to obtain methionine and 2-hydroxy-4-(methylthio)butanoic acid at a high yield, it is preferable to determine the order of supplying the oxide catalyst containing cerium and 3-(methylthio)propionaldehyde so that they are contacted with each other in the presence of the compound containing cyanide ion and ammonia or the compound containing ammonium ion (in particular, the compound containing cyanide ion).

This is because, when the oxide catalyst containing cerium and 3-(methylthio)propionaldehyde are contacted with each other in the absence of the compound containing cyanide ion and ammonia or the compound containing ammonium ion, the catalyst is poisoned and deactivated by the aldehyde; as a result, when the compound containing cyanide ion and ammonia or the compound containing ammonium ion are subsequently supplied, the reactivity is low, thereby decreasing the yield of the target compounds (4) and (7).

Therefore, the order of addition is preferably such that, for example, after the oxide catalyst containing cerium, the compound containing cyanide ion, ammonia or the compound containing ammonium ion, and water are mixed, the mixture is mixed with 3-(methylthio)propionaldehyde.

Further, to increase the yield of methionine (4), the order of addition is preferably such that, after the oxide catalyst containing cerium is mixed with ammonia or the compound containing ammonium ion and the compound containing cyanide ion, the mixture is mixed with 3-(methylthio)propionaldehyde. More specifically, for example, by mixing the oxide catalyst containing cerium with water, subsequently adding the compound containing cyanide ion thereto, further adding ammonia or the compound containing ammonium ion, and, finally, adding 3-(methylthio)propionaldehyde, it is possible to obtain methionine at a high yield.

Further, to increase the yield of 2-hydroxy-4-(methylthio) butanoic acid (7), the order of addition is preferably such that, after the oxide catalyst containing cerium is mixed with the compound containing cyanide ion and 3-(methylthio) propionaldehyde, the mixture is mixed with ammonia or the compound containing ammonium ion. More specifically, for example, by mixing the oxide catalyst containing cerium with water, subsequently adding the compound containing cyanide ion thereto, further adding 3-(methylthio)propionaldehyde, and, finally, adding ammonia or the compound containing ammonium ion, it is possible to obtain 2-hydroxy-4-(methylthio)butanoic acid at a high yield. An example is shown in Example 4.

Generally, the step of mixing the oxide catalyst containing cerium, 3-(methylthio)propionaldehyde, the compound containing cyanide ion, ammonia or the compound containing ammonium ion, and water may be performed in a single vessel. Generally, after the mixing, the reaction is performed in the same reaction vessel. Alternatively, after the mixing in a vessel, the resulting mixture may be transferred to a different reaction vessel to be subjected to a reaction. Further, it is also possible that two or more components selected from the oxide catalyst containing cerium, 3-(methylthio)propionaldehyde, the compound containing cyanide ion, ammonia or the compound containing ammonium ion, and water, are first mixed, and the mixture is then supplied to a vessel to be mixed with the rest of the compounds. For example, it is possible that the oxide catalyst containing cerium is first mixed with water, and then the mixture is supplied to a vessel, or that the compound containing cyanide ion and ammonia or ammonium ion are mixed first and then the mixture is supplied to a vessel.

The reaction may be performed after 3-(methylthio)propionaldehyde, the compound containing cyanide ion, ammonia or the compound containing ammonium ion, and water are mixed. The reaction temperature is generally 0 to 300° C., preferably 0 to 150° C., and most preferably 40 to 110° C. The reaction may be performed under an increased pressure as necessary, preferably at 0.1 to 2 MPa, and more preferably at 0.2 to 0.5 MPa, based on absolute pressure. Further, the reaction conditions, such as temperature, pressure, and the like, may be changed stepwise or successively during the reaction. This manufacturing step may be performed in any of a continuous reactor, a semicontinuous reactor, and a batch reactor.

The catalyst in which the activity is decreased by the reaction may be reused after being separated from the reaction mass and regenerated. As a method for regeneration, washing or heat treatment can be adopted. Washing can be performed with, for example, water, acid, alkali, an organic solvent, and the like. A heat treatment is usually performed under the atmosphere of an oxidizing gas, such as air, an inert gas such as nitrogen or argon, a reducing gas such as hydrogen, carbon dioxide, steam, or the like. Of these, the heat treatment is preferably performed under the atmosphere of an oxidizing gas. Further, the temperature of the heat treatment is preferably 200 to 800° C., and more preferably 300 to 600° C. These methods of washing and heat treatment may be combined.

EXAMPLES

The present invention is described in more detail below with reference to Examples. However, the present invention is not limited only to these Examples.

Example 1

12.1 g of cerium oxide (Daiichi Kigenso Kagaku Kogyo Co., Ltd.) and 60.8 g of water were placed in a three-necked flask equipped with a stirrer and a thermometer, and the mixture was cooled to 10° C. or lower in an ice bath; thereafter, 5.7 g of hydrogen cyanide, 35.0 g of 28 wt % aqueous ammonia, and 20.1 g of 3-(methylthio)propionaldehyde were successively added, and the mixture was stirred in a water bath for six hours at 75° C. Thereafter, the mixture was cooled, and the cerium oxide was removed by a membrane filter, followed by washing with water. The resulting reaction fluid was analyzed by liquid chromatography. The results revealed that the conversion of 3-(methylthio)propionaldehyde was 100%, that the yield of methionine was 48.0%, and that the yield of 2-hydroxy-4-(methylthio)butanoic acid was 49.6%. Further, as for the intermediates, the yield of 2-amino-4-(methylthio)butanamide was 0.6%, and the yield of 2-hydroxy-4-(methylthio) butanamide was 1.7%.

Example 2

12.1 g of cerium oxide (Daiichi Kigenso Kagaku Kogyo Co., Ltd.) and 74.6 g of water were placed in a three-necked flask equipped with a stirrer and a thermometer, and the mixture was cooled to 10° C. or lower in an ice bath; thereafter, 5.7 g of hydrogen cyanide, 15.2 g of 28 wt % aqueous ammonia, and 20.0 g of 3-(methylthio)propionaldehyde were successively added, and the mixture was stirred in a water bath for six hours at 75° C. Thereafter, the mixture was cooled, and the cerium oxide was removed by a membrane filter, followed by washing with water. The resulting reaction fluid was analyzed by liquid chromatography. The results revealed that the conversion of 3-(methylthio)propionaldehyde was 100%, that the yield of methionine was 36.6%, and that the yield of 2-hydroxy-4-(methylthio)butanoic acid was 58.5%. Further, as for the intermediates, the yield of 2-amino-4-(methylthio)butanamide was 1.3%, and the yield of 2-hydroxy-4-(methylthio) butanamide was 3.5%. In contrast to Example 1, by reducing the amount of ammonia, the yield of 2-hydroxy-4-(methylthio)butanoic acid relative to methionine was increased.

Example 3

12.2 g of cerium oxide (Daiichi Kigenso Kagaku Kogyo Co., Ltd.) and 19.7 g of water were placed in a three-necked flask equipped with a stirrer and a thermometer, and the mixture was cooled to 10° C. or lower in an ice bath; thereafter, 5.7 g of hydrogen cyanide, 70.0 g of 28 wt % aqueous ammonia, and 20.0 g of 3-(methylthio)propionaldehyde were successively added, and the mixture was stirred in a water bath for six hours at 75° C.

Thereafter, the mixture was cooled, and the cerium oxide was removed by a membrane filter, followed by washing with water. The resulting reaction fluid was analyzed by liquid chromatography. The results revealed that the conversion of 3-(methylthio)propionaldehyde was 100%, that the yield of methionine was 52.6%, and that the yield of 2-hydroxy-4-(methylthio)butanoic acid was 44.3%. Further, as for the intermediates, the yield of 2-amino-4-(methylthio) butanamide was 0.8%, and the yield of 2-hydroxy-4-(methylthio)butanamide was 2.2%. In contrast to Example 1, by increasing the amount of ammonia, the yield of methionine relative to 2-hydroxy-4-(methylthio)butanoic acid was increased.

Example 4

12.2 g of cerium oxide (Daiichi Kigenso Kagaku Kogyo Co., Ltd.) and 54.7 g of water were placed in a three-necked flask equipped with a stirrer and a thermometer, and the mixture was cooled to 10° C. or lower in an ice bath; thereafter, 5.8 g of hydrogen cyanide, 20.1 g of 3-(methylthio)propionaldehyde, and 34.9 g of 28 wt % aqueous ammonia were successively added, and the mixture was stirred in a water bath for six hours at 75 C. Thereafter, the mixture was cooled, and the cerium oxide was removed by a membrane filter, followed by washing with water. The resulting reaction fluid was analyzed by liquid chromatography. The results revealed that the conversion of 3-(methylthio)propionaldehyde was 100%, that the yield of methionine was 34.9%, and that the yield of 2-hydroxy-4-(methylthio)butanoic acid was 62.1%. Further, as for the intermediates, the yield of 2-amino-4-(methylthio)butanamide was 0.5%, and the yield of 2-hydroxy-4-(methylthio) butanamide was 2.4%.

Example 5 (Separation of Methionine and Liquid Methionine)

Cerium oxide was removed from the reaction fluid obtained in Example 3; thereafter, the reaction fluid was condensed and cooled to crystallize methionine. By filtering it with a membrane filter, followed by washing with water, a solid methionine was obtained. The yield of methionine was about 20 to 50% of the raw material, i.e., 3-(methylthio) propionaldehyde. By condensing the filtrate obtained by filtration, a liquid methionine having a high concentration was obtained.

TABLE 1

|  |  |  | Example 1 | Example 2 | Example 3 | Example 4 |
|---|---|---|---|---|---|---|
| Catalyst |  |  | $CeO_2$ | $CeO_2$ | $CeO_2$ | $CeO_2$ |
| Reaction Temperature |  | ° C. | 75 | 75 | 75 | 75 |
| Reaction Time |  | h | 6 | 6 | 6 | 6 |
| Amount | Ultrapure Water | g | 60.8 | 74.6 | 19.7 | 54.7 |
|  | Catalyst | g | 12.1 | 12.1 | 12.2 | 12.2 |
|  | Hydrogen Cyanide | g | 5.7 | 5.7 | 5.7 | 5.8 |
|  | 28 wt % Aqueous Ammonia | g | 35.0 | 15.2 | 70.0 | 34.9 |
|  | 3-(methylthio) propionaldehyde | g | 20.1 | 20.0 | 20.0 | 20.1 |
| Conversion of 3-(methylthio)propionaldehyde |  | % | 100.0 | 100.0 | 100.0 | 100.0 |
| Yield | (1) Methionine | % | 48.0 | 36.6 | 52.6 | 34.9 |
|  | (2) 2-hydroxy-4-(methylthio)butanoic acid | % | 49.6 | 58.5 | 44.3 | 62.1 |
|  | (3) 2-amino-4-(methylthio)butanamide | % | 0.6 | 1.3 | 0.8 | 0.5 |
|  | (4) 2-hydroxy-4-(methylthio)butanamide | % | 1.7 | 3.5 | 2.2 | 2.4 |
|  | Final Product((1) + (2)) | % | 97.6 | 95.1 | 96.9 | 97.0 |
|  | Valuable Components ((1) to (4)) | % | 99.9 | 99.9 | 99.9 | 99.9 |

INDUSTRIAL APPLICABILITY

The production method of the present invention enables simple production of methionine and/or 2-hydroxy-4-(methylthio)butanoic acid at a high yield using 3-(methylthio) propionaldehyde as a raw material.

The invention claimed is:

1. A method for producing methionine and 2-hydroxy-4-(methylthio)butanoic acid, comprising contacting
    an oxide catalyst containing cerium,
    3-(methylthio)propionaldehyde,
    a compound containing cyanide ion, ammonia or a compound containing ammonium ion, and
    water
with each other,
    wherein the amount of the oxide catalyst containing cerium is, in a cerium amount, 0.02 to 1.5 moles, per mole of 3-(methylthio)propionaldehyde.

2. The method according to claim 1, wherein the oxide catalyst containing cerium is at least one oxide selected from cerium oxides and oxide solid solutions containing cerium.

3. The method according to claim 1, wherein the compound containing cyanide ion is hydrogen cyanide.

4. The method according to claim 1, wherein ammonia or the compound containing ammonium ion is at least one member selected from aqueous ammonia, liquid ammonia, and ammonia gas.

5. The method according to claim 1, wherein the reaction temperature is 40 to 110° C.

6. The method according to claim 1, wherein the oxide catalyst containing cerium, 3-(methylthio)propionaldehyde, hydrogen cyanide, ammonia, and water are contacted with each other in a single vessel.

7. The method according to claim 1, wherein the oxide catalyst containing cerium and 3-(methylthio)propionaldehyde are contacted with each other in the presence of the compound containing cyanide ion and ammonia or the compound containing ammonium ion.

8. The method according to claim 1, wherein, after the oxide catalyst containing cerium, the compound containing cyanide ion, ammonia or the compound containing ammonium ion, and water are mixed, the mixture is mixed with 3-(methylthio)propionaldehyde.

* * * * *